United States Patent
Glowacki et al.

(10) Patent No.: US 9,638,664 B2
(45) Date of Patent: May 2, 2017

(54) METHOD OF ANALYZING A MATERIAL

(75) Inventors: Piotr Glowacki, Umina Beach (AU); Guy James Reynolds, Helensburgh (AU)

(73) Assignee: DBD Innovations Pty Ltd, Sutherland, NSW (AU)

( * ) Notice: Subject to any disclaimer, the term of this patent is extended or adjusted under 35 U.S.C. 154(b) by 306 days.

(21) Appl. No.: 13/994,086

(22) PCT Filed: Mar. 6, 2012

(86) PCT No.: PCT/AU2012/000228
§ 371 (c)(1),
(2), (4) Date: Jul. 1, 2013

(87) PCT Pub. No.: WO2012/155174
PCT Pub. Date: Nov. 22, 2012

(65) Prior Publication Data
US 2013/0285639 A1  Oct. 31, 2013

(30) Foreign Application Priority Data

May 13, 2011 (AU) ................................ 2011901805
Sep. 9, 2011 (AU) ................................ 2011903703

(51) Int. Cl.
*G01N 27/62* (2006.01)
*G01N 27/70* (2006.01)
(Continued)

(52) U.S. Cl.
CPC ............ *G01N 27/62* (2013.01); *A61C 19/04* (2013.01); *G01N 27/70* (2013.01);
(Continued)

(58) Field of Classification Search
CPC ....... G01N 27/62; G01N 27/70; H05H 1/2406
(Continued)

(56) References Cited

U.S. PATENT DOCUMENTS

2003/0062919 A1* 4/2003 Vargas ................. G01N 27/205
324/762.1
2005/0145174 A1* 7/2005 Chaleix ................. B08B 7/0035
118/723 R
(Continued)

FOREIGN PATENT DOCUMENTS

WO   WO 03/052432 A2   6/2003

OTHER PUBLICATIONS

Na Na, Mengxia Zhao, Sichun Zhang, Chengdui Yang, Xinrong Zhang, Development of a Dielectric Barrier Discharge Ion Source for Ambient Mass Spectrometry, Oct. 2007, Journal of the American Society for Mass Spectrometry, vol. 18, Issue 10, pp. 1-4.*
(Continued)

*Primary Examiner* — Son Le
*Assistant Examiner* — Brent J Andrews
(74) *Attorney, Agent, or Firm* — Kilpatrick Townsend & Stockton LLP

(57) ABSTRACT

A method of material analysis, including; placing an electrode in proximity to the material; applying a voltage signal to generate plasma, preferably Dielectric Barrier Discharge in Air, between the material and the electrode; moving the electrode relative to the surface; monitoring an electrical signal associated with the microdischarge; and detecting a change in a physical characteristic of the material through variation in the monitored signal.

20 Claims, 7 Drawing Sheets

(51) Int. Cl.
  *H05H 1/24* (2006.01)
  *A61C 19/04* (2006.01)
(52) U.S. Cl.
  CPC ... *H05H 1/2406* (2013.01); *H05H 2001/2412* (2013.01); *H05H 2245/122* (2013.01)
(58) Field of Classification Search
  USPC ......... 324/76.65, 76.76, 464, 467, 515, 557, 324/71.1
  See application file for complete search history.

(56) References Cited

U.S. PATENT DOCUMENTS

| | | | |
|---|---|---|---|
| 2005/0178749 A1 | 8/2005 | Yamazaki et al. | |
| 2009/0297409 A1* | 12/2009 | Buchanan et al. | 422/186.29 |
| 2009/0315573 A1* | 12/2009 | Arndt et al. | 324/693 |
| 2010/0229629 A1* | 9/2010 | Egami et al. | 73/28.01 |
| 2010/0327873 A1* | 12/2010 | Dorf et al. | 324/464 |

OTHER PUBLICATIONS

International Search Report and Written Opinion of PCT/AU2012/000228 mailed on May 21, 2012, 10 pages.

* cited by examiner

METHOD OF ANALYZING A MATERIAL

RELATED APPLICATIONS

The present application claims priority from Australian Patent Application Number 20011903703 and Australian Patent Application Number 2011901805, the contents of which are incorporated herein by reference.

FIELD OF THE INVENTION

The present invention relates to a method of analyzing a material.

BACKGROUND OF THE INVENTION

The invention takes advantage of known properties of atmospheric pressure glow discharge. Atmospheric pressure glow discharge (APGD) has numerous applications due to operating at strongly non-equilibrium conditions in various gases, including air, at reasonably high power levels.

One particular form of APGD discharge is a dielectric barrier discharge (DBD), which is particularly interesting as it does not need sophisticated power supplies or circuitry.

Dielectric-barrier discharge (DBD) is the electrical discharge between two electrodes separated by an insulating dielectric barrier.

DBD plasma is typically obtained when the electrodes are separated by a gap of some millimeters and excited by alternating high voltage with frequency in the range 1 Hz-100 kHz. Typically in air, the DBD is formed by a large number of separate current filaments referred to as microdischarges. The microdischarges have a typical diameter in the range of 100 micrometers. These microdischarges have a complex dynamic structure and are formed by channel streamers that usually repeatedly strike at the same place as the polarity of the applied voltage changes, thus appearing as bright filaments.

In certain cases though, such as when the applied high voltage rise time is extremely short (for example dV/dt>1 kV/ns), the microfilaments may not form any stable pattern, and the discharge may appear uniform.

The persistence of streamers to strike at the same place of previous microstreamers is due to memory effect. The memory effect is associated with charge deposited on the dielectric barrier, as well as on residual charges and excited species in the microdischarge channel.

The DBD microstreamer pattern will generally have a regular pattern structure for any given material and a visible discharge may be observed as a result of the energy release from the plasma generated in the microstreamers.

The microstreamers are, however, extremely short lived—the avalanche to streamer transition generally takes about 10 ns, followed by the extinction of the microstreamers. The extinction voltage of the microdischarges is not far below the voltage of their ignition. Charge accumulation on the surface of the dielectric barrier reduces the electric field at the location of a microdischarge, which results in current termination within tens of nanoseconds after breakdown. The short duration of current in the microdischarges leads to low heat dissipation and, as such, the DBD plasma remains substantially non-thermal.

The characteristics of the DBD render the process suitable for many industrial applications such as ozone generation, medical applications, waste treatment, pollution control and surface treatment to promote wettability, printability and adhesion. Importantly, the DBD is non-destructive as there is no electrical arc generation between the electrodes.

As alternative to DBD, the dielectric barrier can be replaced by a highly resistive barrier. This may be accomplished by including one or more high value resistors in the circuit, or making the electrode of highly resistive material. This mode of operation is usually called RBD (resistive barrier discharge).

OBJECT OF THE INVENTION

The present invention seeks to take advantage of microdischarge characteristics for material analysis.

SUMMARY OF THE INVENTION

In accordance with the present invention, there is provided a method of analysing a material, including:
  placing an electrode in proximity to the material;
  applying a voltage signal to generate microdischarges between the material and the electrode;
  moving the electrode relative to the surface;
  monitoring a signal associated with the microdischarge;
  detecting a change in a physical characteristic of the material through variation in the monitored signal.

Preferably, the change in physical characteristic represents one of a surface defect, a change in surface coating, variation of material structure or composition, or a topographical change.

Preferably, the method includes providing the electrode as a portable dielectric electrode.

Preferably, the method includes identifying a surface defect as a result of detecting the topographical feature.

Preferably, the method includes applying dielectric barrier discharge (DBD) between the material and the electrode.

Preferably, the method includes tuning circuitry used to apply a signal to the electrode, in order to generate the DBD only when the electrode is proximate the material and adjacent the change in physical characteristic.

Preferably, the method includes applying the electrode to teeth and the topographical feature represents a cavity in the tooth, non-cavitated lesion, crack, or void between the tooth and a dental filling, crown, bridge or similar.

Preferably, the method includes monitoring radiation emitted by the microdischarge pattern and identifying a fluctuation in the emitted radiation to indicate a change in physical characteristics of the material.

BRIEF DESCRIPTION OF THE DRAWINGS

The invention is more fully described, by way of non-limiting example only, with reference to the accompanying drawings, in which.

DETAILED DESCRIPTION OF THE INVENTION

Figure 1:
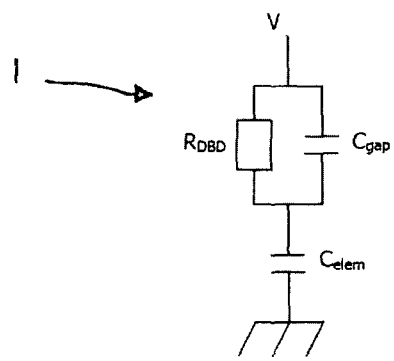
FIG. 1 is a circuit diagram.

FIG. 1 shows a simplified circuit diagram 1 illustrating the general principles of the invention, where: V represents a pulsed high voltage; Cgap is the capacitance of the gap between the electrode and material to be tested; Celem represents the Capacitance of the material; and RDBD represents the resistance of DBD discharge. If the tested element is of sufficiently high dielectric constant, the ground connection is not necessary and the element may be at floating potential.

When the capacitance of the tested material varies due to properties of its surface topography, structure, composition or coating, the impedance of the effective resistance changes. This causes changes to the discharge so the RDBD is effected too and the analysis of the circuit becomes complex.

However, such variation means the current signal, for example, of the circuit can be monitored for and when such a variation does occur this will represent a corresponding change in the material surface structure or composition.

Figure 2:
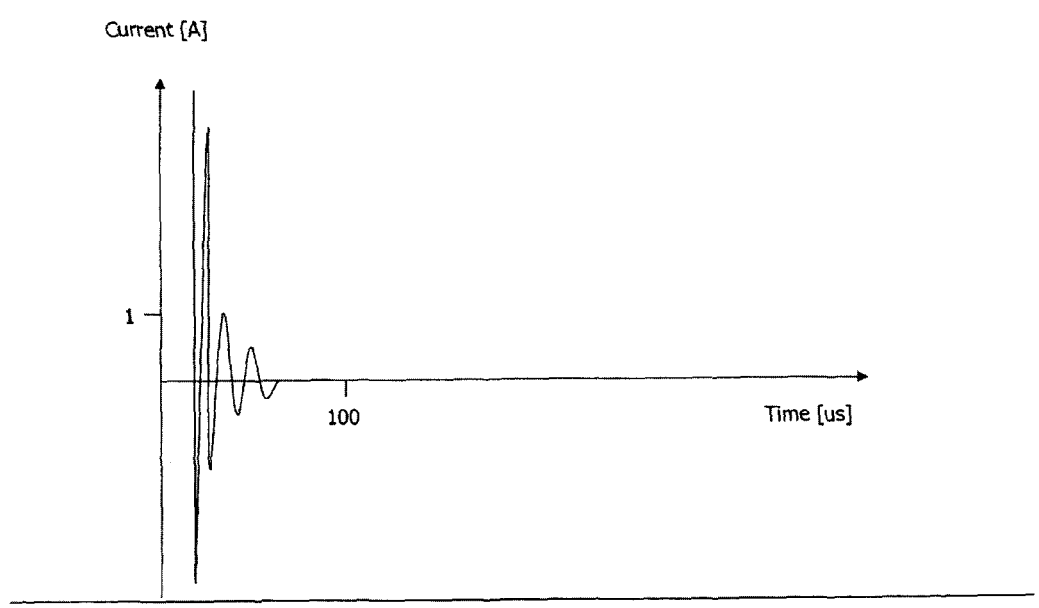
FIG. 2 is a signal representing discharge in the circuit of FIG. 1.

FIG. 2 shows a typical plot of current discharge versus time, when pulsed power supply is used. Changes to the material characteristics would alter the amplitude, frequency and/or decay time of the oscillations of the signal.

Figure 3:
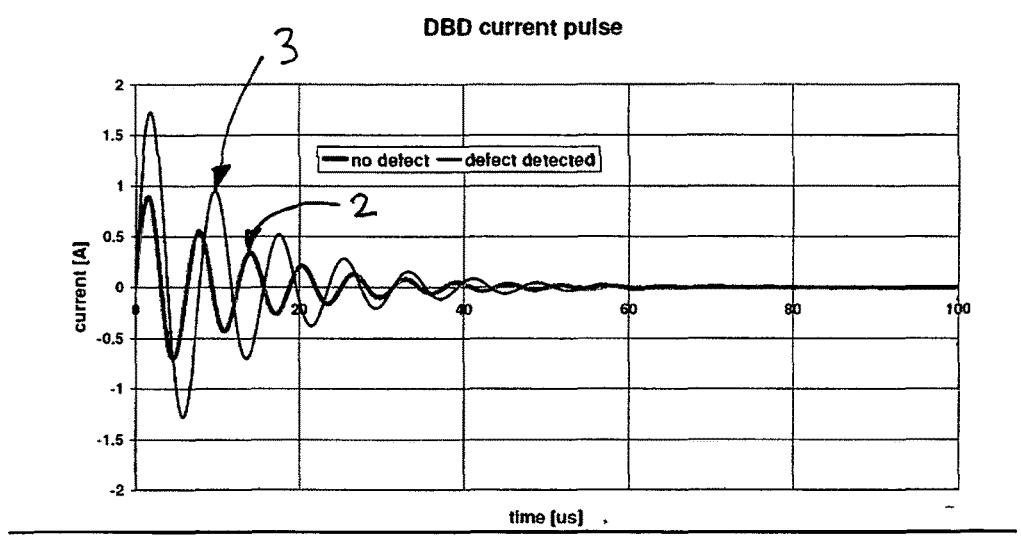
FIG. 3 is a plot showing variation in the signal.

By way of illustration, FIG. 3 shows a current signal 2, which represents a standard DBD pulse for the circuit shown in FIG. 1, when DBD is applied to the material. Another current signal 3 represents the DBD pulse when a variation in the physical characteristics of the material is detected. In this instance, the amplitude, frequency and decay rate of the signal 3 are substantially changed relative to the first signal 2, thereby indicating a material defect or the like.

Figure 4:
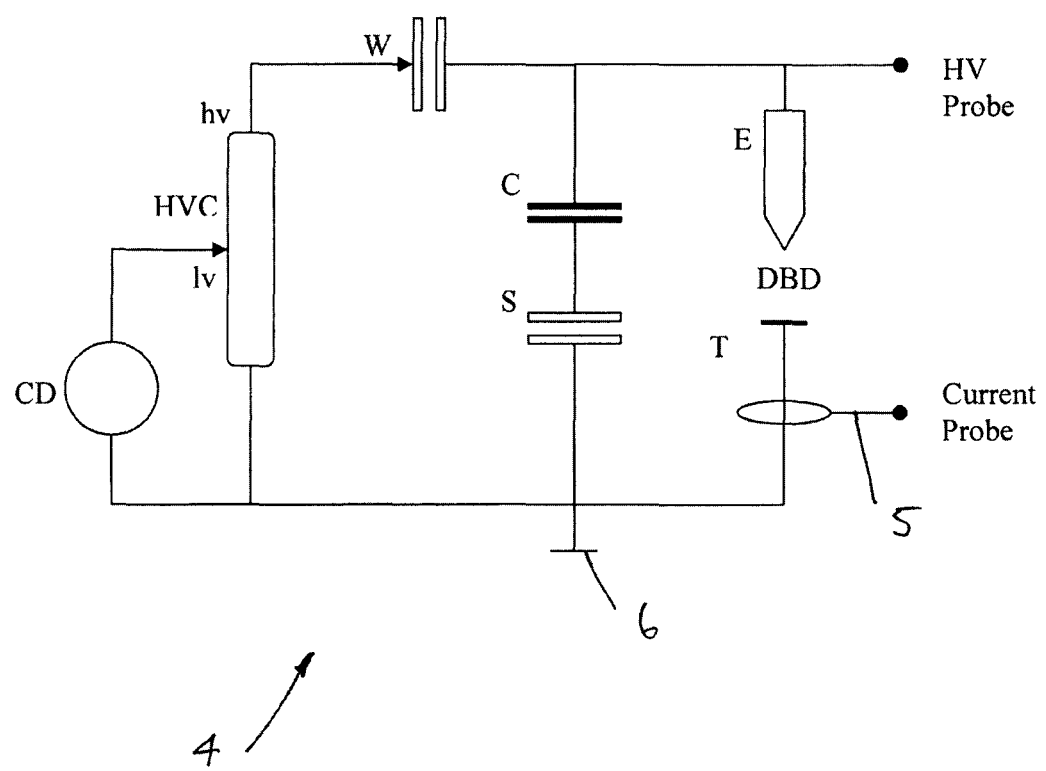
FIG. 4 is a circuit diagram with a probe.

Turning now to FIG. 4, another circuit 4 is illustrated. The circuit includes a high voltage ignition coil driver CD which controls the voltage output from a high voltage coil HVC, between a high voltage terminal hv and a low voltage terminal Iv. An electrode E and capacitor C are connected in parallel to the high voltage coil though a spark gap W. A second spark gap S is provided between the capacitor and ground. T represents the tested material and DBD indicates the location of the dielectric barrier discharge. A high voltage probe and/or current probe 5 is provided to monitor the signal between the material and ground 6.

With regard to FIG. 5, a similar circuit 7 to that described with reference to FIG. 4 is illustrated and like parts are denoted in a similar manner. In this case, a resistive load has been added into the circuit between the test material and ground and an oscilloscope DSO is applied directly between the material T and the ground side of R. The resistance may be of any value. The high voltage probe and/or current probe is not required in this configuration as the signal is monitored by the oscilloscope.

Figure 5:
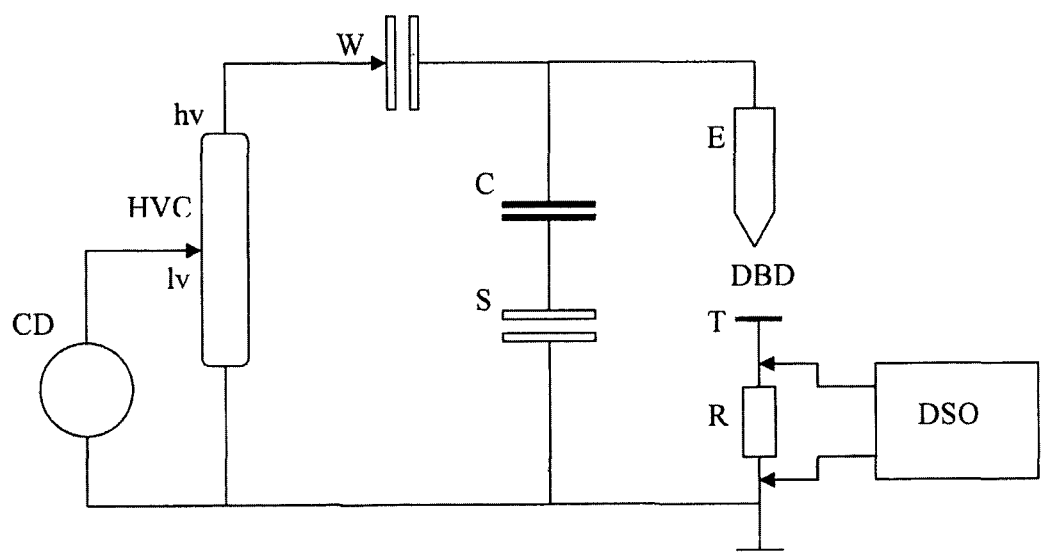
FIG. 5 is a circuit diagram with an oscilloscope.
Figure 6:
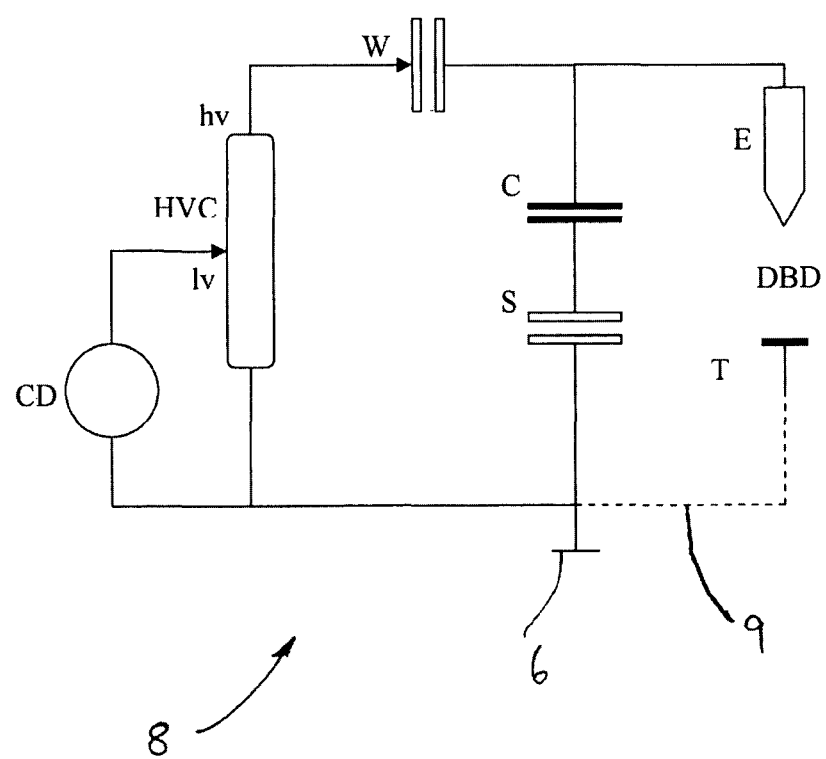
FIG. 6 is another circuit diagram for visual tests.

With regard to FIG. 6, a similar circuit 8 to that described with reference to FIG. 5 is illustrated, where like parts are denoted in like manner. In the circuit of FIG. 6, the oscilloscope has been dispensed with. This corresponds to a circuit where any variation in the microdischarge pattern is monitored by way of fluctuations in the emitted radiation, which is preferably visually discernible. The material to be tested is grounded or at a floating potential. The dashed line 9 indicates an optional ground 6.

Figure 7:
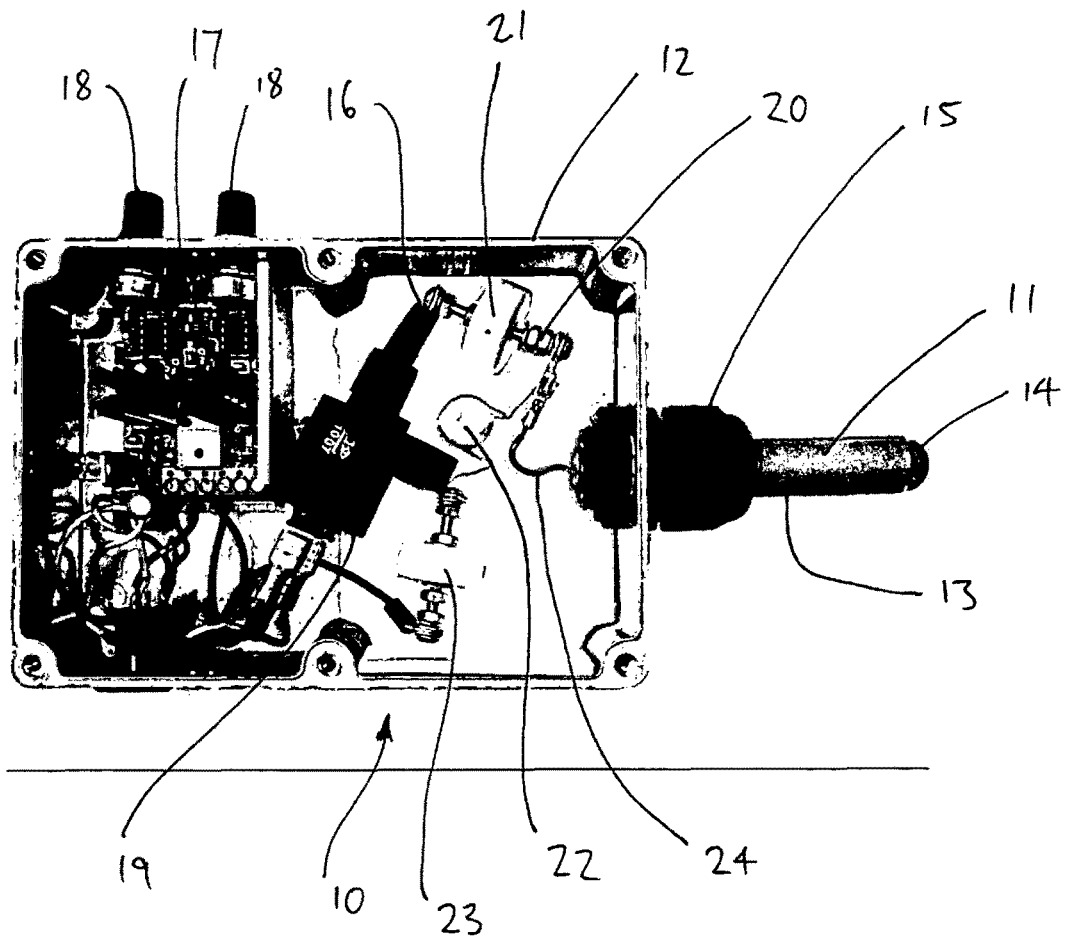
FIG. 7 is an illustration of a test device.

Referring now to FIG. 7, a test device 10 is shown. The device 10 includes an electrode 11 which projects externally of a housing 12. The electrode 11 is a formed of a rigid conductive member 13 covered with a dielectric covering 14. The electrode 11 can, of course, be formed as a flexible electrode, if needed.

The dielectric may be formed of one or more dielectric coatings. In that regard, the dielectric may be formed of any suitable material such as ceramics, Kapton tape, quartz, glass or the like, with a high electric breakdown strength and low dielectric loss.

The electrode 11 is detachably mounted to the housing 12 via a screw-threaded collar 15 and is electrically connected into a circuit 16, which is wired generally in accordance with FIG. 6.

More particularly, the circuit 16 is provided with a high voltage driver PCB 17, which can be adjusted or tuned via control knobs 18 to set a voltage output from high voltage coil 19. The circuit 16 has a loop 20 which includes spark gap W, as indicated by reference number 21, capacitor 22 and spark gap S, represented by reference number 23. The electrode 11 is electrically connected, via lead 24, into the circuit 16 between the spark gap 21 and the capacitor 22. The spark gaps 21, 23 are provided for the purpose of producing short energy pulses through the circuit, to the electrode 11.

The device 10 has been described simply for the purpose of illustration and either of the other circuits of FIGS. 4 and 5 could instead be used provided the electrode is capable of generating a microdischarge when placed in close proximity to a material to be tested.

Regardless of the particular circuit used, the device is preferably tunable, such as by knobs 18, by adjusting the properties of the driving impulse from the high voltage coil driver, such as the amplitude, frequency, duty cycle, waveform, etc. More crudely, the spark gaps, which define the distance between the spark gap electrodes, can be adjusted.

The device 10 could also be tuned by changing the DC power supply voltage of the driver and/or coil driving voltage. Alternatively, other elements of the circuit could be varied such as the probe, coil or capacitor, which would also effect the behavior of the device.

By tuning the device 10, it should be possible to generate a discharge only when a particular variation in material properties is present to indicate a specific defect or change in impedance. This has an advantage of allowing easy identification of a change in the material characteristics. The discharge can also provide a convenient visual indication of the location of a material fault or the like.

Importantly though, the discharge will always be a pattern of microdischarges, characteristic of DBD so that there is no spark generation which might cause damage. As such, the invention is non-destructive and safe to use. To protect against spark generation, the electrode is coated in a dielectric material, which ensures the discharge is always DBD.

With the above in mind, the device is operated with short pulses of high voltage and long breaks in between, which means the duty cycle is low compared to a continuous sinusoidal signal. Accordingly, the power required to generate a DBD is minimal, which further renders the device safe for use in sensitive applications such as in the medical field. The device may be battery powered and portable.

Figure 8:
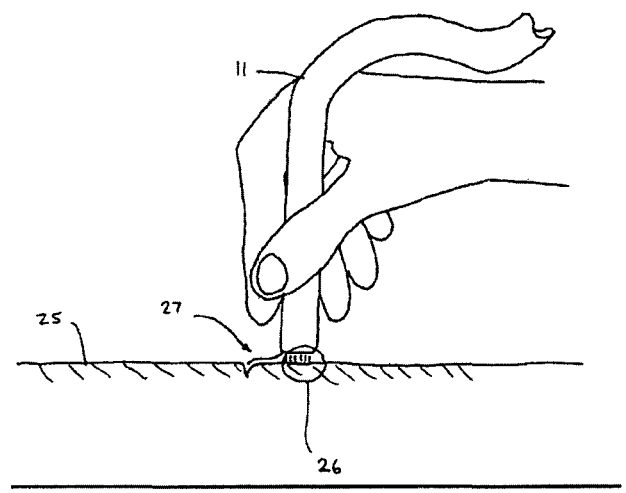
FIG. 8 is a diagrammatic representation illustrating the method of the invention.

Turning now to FIG. 8, the methodology of the invention is explained in more detail. As shown, the electrode 11 is placed in close proximity to the material 25 to be tested and a signal is applied from the device to generate a microdischarge pattern in the air above the material, indicated by reference numeral 26.

The electrode 11 can then be moved relative to the material 25 and any change in the material characteristics will give rise to a variation in the monitored signal, such as represented in FIG. 3. In the case where the discharge pattern is being monitored visually, a visual fluctuation in the pattern should be observable. For example, a microdischarge filament 27 will be clearly seen to jump from the regular discharge pattern, indicating a change in the material characteristics, such as in surface topography, surface coating or surface imperfection.

The electrode 11 is illustrated as being hand held but the electrode could instead be mounted for machine manipulation or, in any case, fixed and the material instead moved relative to the electrode. The electrode 11 is also shown as being flexible for easy manipulation but can instead be rigid such as shown in FIG. 7, as required, and detachable from the device 10. The electrode 11 can also be of any suitable shape, as dictated by the testing material or environment.

The described circuits and test device 10 have been set up to operate with filamental DBD, however, any other similar type of discharge will suffice. For example, a uniform DBD discharge or any other suitable form of atmospheric pressure glow discharge will suffice.

In either case, the device 10, or at least the electrode 11, is preferably portable and ideally hand held so that the material analysis can be done for any given surface such as for finding cavities or micro-cracks in teeth. The methodology can be readily up-scaled for industrial use and applied to monitor any material or defects such as to check for structural fatigue, corrosion or fractures in protective coatings or paints used for aircraft, marine, automotive, tools, machinery, etc.

Example 1—Insulated Coating

The method of the invention may be applied to check an insulated coating over a conductive substrate using near atmospheric pressure glow discharge and preferably DBD.

In a preferred arrangement, the high voltage ignition coil driver produces impulse square wave signals at a typical frequency range of 10 Hz to 1 MHz. When the high voltage driver is activated, and the electrode is placed near the tested element, a DBD discharge ignites. Typically, the distance between the electrode and the surface of the tested element is between 0 and 10 mm, while the amplitude of the discharge voltage is in a range of 1 to 50 kV.

The preferred method of testing relies on the discharge current changing as the impedance of the tested material or coating changes.

The changes may occur as a result of variations in thickness, surface adhesion, dielectric constant, porosity, surface roughness, contamination, etc.

Since the DBD in air usually consists of a number of plasma filaments between the electrode and the tested coating, and typical diameter of a filament is in a range of 100 micrometers, even very small cracks and gaps in the insulation can be detected.

In addition, the DBD may ignite a capillary plasma electrode discharge (CPED) in the bulk of the tested coating, which could enhance resolution and enable material porosity measurements.

As such, application of the method of the present invention, allows faults or changes in characteristics of an insulating coating to be readily identified.

Example 2—Dental Application

For a dental application, the method of the invention can be used to test integrity of tooth enamel using near atmospheric pressure glow discharge and, most preferably, DBD.

The method relies on discharge properties changing as a result of the impedance of the tested area varying. The changes may occur due to variations in thickness, porosity, surface roughness, contaminants, etc. In particular, the electrical impedance of thinned, fractured or de-mineralized tooth enamel is lower than that of healthy, intact enamel. This enables detection and activity assessment of early stage, non-cavitated caries lesions, which is essential for effective diagnosis and treatment.

The test is accomplished by applying alternating high voltage between the powered electrode of the device and the tested, dry tooth, in such a way that the atmospheric pressure glow discharge is ignited and maintained in air, while a signal such as an electric current associated with the discharge, impedance and/or discharge frequency are being monitored.

The operating parameters described with reference to Example 1 are also relevant to this Example.

The low temperature and non-destructive nature of the discharge renders this methodology ideal for safe use on patients.

Once a defect has been located in the enamel, the discharge may also be used to clean the site, in and around the enamel.

In the dental application, it is also possible to detect micro-cracks, non-cavitated lesions, or voids between the teeth and dental fillings, crowns, bridges or similar. Such defects might not yet be visible to the naked eye. As such, the method can provide for considerably advance dental care, as compared to that currently available.

To further simplify detection of faults in teeth, the device 1 can also be tuned so that the discharge occurs only when the electrode is over a reduced impedance site, which indicates the location of deteriorated enamel or a fault. The discharge may also be visible so that a dental technician is provided with a clear visual indication of the position of the site.

The above Examples 1 and 2 have been provided for illustrative purposes only and the invention clearly has application to testing or analyzing almost any material where a discharge pattern can be established at its surface.

As may be appreciated from the above, the method of the present invention, particularly when using DBD, has a number of advantages in so far as the method is: non-destructive; able to detect micro-sized defects such as micro-cracks; inherently scalable, with a detachable or flexible probe of arbitrary shape; transportable; capable of being conducted on battery power; safe; and simple and inexpensive.

LIST OF PARTS

1. Circuit;
2. Signal;
3. Signal;
4. Circuit;
5. Probe;
6. Ground;
7. Circuit;
8. Circuit;
9. Dashed line;
10. Device;
11. Electrode;
12. Housing;
13. Conductive member
14. Dielectric;
15. Collar;
16. Circuit;
17. High voltage driver;
18. Knobs;
19. Coil;

20. Loop;
21. Spark gap;
22. Capacitor;
23. Spark gap;
24. Lead;
25. Material;
26. Pattern;
27. Microdischarge filament.

The invention claimed is:

1. A method of analysing a material, including;
placing a dielectric coated electrode in proximity to the material;
applying a voltage signal to generate a dielectric barrier discharge (DBD) between the material and the electrode;
moving the electrode relative to the surface;
monitoring a signal associated with the microdischarge; and
detecting a change in a physical characteristic of the material through variation in the monitored signal.

2. The method of claim 1, wherein the method includes tuning circuitry used to apply a signal to the electrode, in order to generate the DBD only when the electrode is proximate the material and adjacent the change in physical characteristic.

3. The method of claim 1, wherein the method includes applying the electrode to teeth and the topographical feature represents a cavity in the teeth.

4. The method of claim 3, used to detect cavitated or non-cavitated caries lesions, micro-cracks, or voids between the teeth and dental fillings, crowns, bridges or similar.

5. The method of claim 1, wherein the change in physical characteristic represents one of a surface defect, a change in surface coating, variation of material structure or composition, or a topographical change.

6. The method of claim 1, wherein the method includes providing the electrode as a portable dielectric electrode.

7. The method of claim 1, wherein the method includes identifying a material defect as a result of detecting a surface defect, a change in surface coating, variation of material structure or composition, or a topographical feature.

8. The method of claim 1, when used to detect characteristics of a dielectric coating.

9. The method of claim 1, wherein the method includes monitoring radiation emitted by the discharge and identifying a fluctuation in the emitted radiation to indicate a change in physical characteristics of the material.

10. The method of claim 9, wherein the fluctuation in the monitored radiation is identified visually through visually observable changes in the DBD pattern, which indicate the location of the change in physical characteristic.

11. The method of claim 1, wherein the dielectric coated electrode comprises a rigid conductive member covered with a dielectric covering.

12. The method of claim 11, wherein the dielectric is characterized by a high electric breakdown strength and low dielectric loss.

13. The method of claim 1, wherein the electrode and a capacitor are connected in parallel to a high voltage coil through a spark gap.

14. The method of claim 1, wherein the dielectric coating the electrode prevents electrical spark formation during the monitoring and detecting.

15. A method of analyzing a material, including;
placing an electrode in proximity to the material;
applying a voltage signal to generate a dielectric barrier discharge (DBD) between the material and the electrode;
moving the electrode relative to the surface;
monitoring a signal associated with the DBD; and
detecting a change in a physical characteristic of the material through variation in the monitored signal, wherein the variation is not associated with termination of the DBD due to spark discharge and is instead representative of an associated change in the DBD when the electrode is adjacent the change in the physical characteristic.

16. The method of claim 15, wherein placing the electrode includes placing a dielectric coated electrode in proximity to the material.

17. A method of analyzing a material, including;
placing an electrode in proximity to the material;
applying a voltage signal to generate a dielectric barrier discharge (DBD) between the material and the electrode;
moving the electrode relative to the surface;
ensuring a dielectric is continuously present between the electrode and the material to avoid any instance of spark discharge between the material and the electrode;
monitoring a signal associated with the DBD; and
detecting a change in a physical characteristic of the material through variation in the monitored signal.

18. The method of claim 17, wherein placing the electrode includes placing a dielectric coated electrode in proximity to the material.

19. A method of analyzing a material, including;
placing an electrode in proximity to the material;
applying a voltage signal to generate a dielectric barrier discharge (DBD) between the material and the electrode;
moving the electrode relative to the surface;
monitoring a signal associated with the DBD; and
detecting a change in a physical characteristic of the material through variation in the monitored signal.

20. The method of claim 19, wherein placing the electrode includes placing a dielectric coated electrode in proximity to the material.

* * * * *